(12) United States Patent
Bendele et al.

(10) Patent No.: US 7,766,979 B2
(45) Date of Patent: Aug. 3, 2010

(54) PHASE TRANSFORMATION IN MOLECULAR SOLIDS

(75) Inventors: Tanja Bendele, Essen (DE); Claudia Weidenthaler, Mülheim an der Ruhr (DE); Michael Felderhoff, Essen (DE)

(73) Assignee: Avantium International B.V., Amsterdam (NL)

( * ) Notice: Subject to any disclaimer, the term of this patent is extended or adjusted under 35 U.S.C. 154(b) by 275 days.

(21) Appl. No.: 10/587,498

(22) PCT Filed: Jan. 26, 2005

(86) PCT No.: PCT/DE2005/000098

§ 371 (c)(1),
(2), (4) Date: Sep. 20, 2006

(87) PCT Pub. No.: WO2005/072699

PCT Pub. Date: Aug. 11, 2005

(65) Prior Publication Data

US 2007/0202024 A1    Aug. 30, 2007

(30) Foreign Application Priority Data

Jan. 28, 2004    (DE) .................. 10 2004 004 122

(51) Int. Cl.
*B28B 3/00*    (2006.01)

(52) U.S. Cl. .............. 23/295 R; 264/239; 264/333
(58) Field of Classification Search ................. 264/333; 430/48; 205/661; 23/295 R
See application file for complete search history.

(56) References Cited

U.S. PATENT DOCUMENTS

2003/0113802 A1 * 6/2003 Matzger et al. ............ 435/7.1

FOREIGN PATENT DOCUMENTS

| JP | 06345992 | * 12/1994 |
| WO | WO 9610539 A1 | * 4/1996 |

OTHER PUBLICATIONS

Landolt-Börnstein—Group III Condensed Matter Numerical Data and Functional Relationships in Science and Technology Ternary Compounds, Organic Semiconductors SpringerLink -book chapter, 10.1007/10717201_539. 2000. Accessed Oct. 21, 2008.*
Hematite information, Webmineral.com Accessed Oct. 21, 2008.*
Brittain, Harry G. "Effects of Mechanical Processing on Phase Compositions". J. Pharm. Sci. 91 (7). 1573-1580. Jun. 27, 2001.*

* cited by examiner

*Primary Examiner*—Stuart Hendrickson
*Assistant Examiner*—Richard M Rump
(74) *Attorney, Agent, or Firm*—Hoffmann & Baron, LLP

(57) ABSTRACT

This invention relates to a method for phase transformation in molecular solids and the use of high-energy mills of said method.

20 Claims, No Drawings

PHASE TRANSFORMATION IN MOLECULAR SOLIDS

CROSS-REFERENCE TO RELATED APPLICATIONS

This application is the National Stage of International Application No. PCT/DE2005/000098, filed Jan. 26, 2005, which claims the benefit of German Application No. DE 10 2004 004 122 9, filed Jan. 28, 2004.

FIELD OF THE INVENTION

The invention relates to a process for inducing and/or accelerating a phase transformation in molecular solids.

BACKGROUND OF THE INVENTION

The processes used almost exclusively for generating defined solid phases of molecular solids are based on crystallization and/or precipitation from solutions, suspensions or dispersions. This is usually done as one of the last purification steps after the synthesis of the appropriate compounds. However, the crystallization conditions/precipitation conditions are also frequently varied in a controlled manner in order to prepare certain polymorphic modifications or amorphous phases of the compounds used in a pure phase or in the form of mixtures of different phases.

Phases shall be understood here to mean not only polymorphs of a chemical compound; instead, also included are pseudopolymorphs (solvates, hydrates), adducts, complexes, salts, cocrystals, which may be present in various phases.

It is also known that phase transformations can be influenced by thermal and/or mechanical conditions. For example, there is a targeted search for metastable phases under defined thermal conditions, for example in highly supercooled melts or by repeated melting and cooling. These processes find use only on the microscale and have therefore to date been, if anything, of scientific interest.

The literature discloses that, specifically in the preparation of medicaments, partial phase transformations are observed time and again in the formulation of the active ingredients and excipients. Particularly in the formulation of the active ingredients, for example, partial phase transformations are a common complaint. This is the case especially when the phase transformation proceeds in an unwanted manner and/or only partially. What are particularly problematic are phase transformations when the product specification is altered inadvertently and the processability, bioavailability, etc., of the corresponding compounds is influenced unfavorably.

The preparation of stable solid phases of molecular compounds is of great significance for various reasons. This is because different crystal forms possess different physical, chemical and biological properties. For example, the thermal properties (melting point, decomposition temperature), the solubility, the stability, the grinding behavior, the compressibility, the bioavailability, the density, the optical properties (NLO properties, color, fluorescence), magnetic properties, the chemical reaction behavior and, for example, the hydrolysis rate can differ significantly from one another.

To date, molecular solids (molecular crystalline or amorphous phases) have been prepared almost exclusively via the route of crystallization and/or precipitation from solutions, suspensions, dispersion, solvent mixtures or mixtures thereof, and also by lyophilization. A great disadvantage of these processes, specifically in the industrial scale sector, is that large amounts of solvents are obtained in the processes.

Moreover, crystal solvates or solvate adducts are formed very frequently and can restrict the usability of the compounds. Particularly in the field of the medicaments industry, there is an interest in producing active ingredients and excipients in stable and solvent-free form.

For the medicaments industry, the preparation of stable phases is particularly relevant, in order to ensure reproducible, lasting product specifications.

In the foods and dyes industry too, there is a need for stable, environmentally friendly, solvent-free and preferably loss-free processes for preparing molecular crystalline phases of the particular compounds; particularly for preparing stable molecular phases.

For health reasons, economic reasons and for reasons of environmental protection, there is therefore a need for a widely applicable stable process which is suitable for phase transformation in molecular solids.

SUMMARY OF THE INVENTION

It is an object of the invention to provide a process for phase transformation of molecular solids which allows the controlled transformation of the solid to another solid crystalline phase.

DETAILED DESCRIPTION OF PREFERRED EMBODIMENTS

The present invention accordingly provides a process for inducing and/or accelerating at least one phase transformation in molecular solids, characterized in that the molecular solid is subjected to a tribochemical treatment.

It has been found that, surprisingly, tribochemical treatment of the solids can induce and/or accelerate a phase transformation. This phase transformation is effected during the tribochemical treatment; further steps or further treatments of the solids are not required.

Tribochemical methods include in particular high-energy grinding and reactive grinding. What is common to the processes mentioned from the field of the tribochemical methods is that they work essentially with the transmission of very high mechanical energies, especially in the form of high kinetic energies. They are summarized as processes which work with the transmission of high kinetic energy (high kinetic processing, HKP).

In the context of the present invention, "molecular solids" are understood in particular to mean crystalline molecular solids, amorphous molecular solids, glasslike molecular solids, solid solutions, liquid-crystalline molecular solids and mixtures thereof, and also molecular compounds present in pasty or highly viscous form. The solids are preferably comprise organic compounds and salts thereof, or consist thereof.

A phase shall be understood to mean not just the phase of the compound; instead, also included are in particular phases of pseudopolymorphs (solvates, hydrates), adducts, complexes, salts, cocrystals, which may in turn be present in various phases.

"Phase" shall be understood to mean the state of the molecular solids in which it is uniform with regard to composition and with regard to physical state.

In particular, phases mean polymorphous phases of molecular compounds, mesophases, amorphous, glasslike, rotatory, nematic, smectic, cholestric, discotic, lyotropic phases of molecular compounds, which may be present even in solid or in pasty, highly viscous or liquid-crystalline form.

The molecular solids consist preferably of pure phases. These phases preferably have a purity above 90%. An essentially pure phase shall be understood to mean a phase having a purity of greater than 80%.

In addition, in particular, a process is provided which induces and/or accelerates a phase transformation in molecular solids by means of transmission of high mechanical energies, especially by transmission of high kinetic energies. The mechanical energy is transmitted, for example, via high impact energies as a result of accelerations achieved in the grinding media which are above 20 G, in particular above 35 G, more preferably above 40 up to 50 G and higher [natural constant G]. Preference is given to transformations to molecular solids in which one crystalline phase is converted to another crystalline phase.

The process according to the invention can be carried out without cooling, which has the advantage that the apparatus setup is simplified and the costs of the process can be minimized. Possible heating of the sample in the course of prolonged grinding times to temperatures above room temperature, i.e. above 20° C., possibly up to 50° C., typically to temperatures between 20 and 40° C., in particular between 20 and 30° C., can, depending on the molecular solids used, lead to more rapid induction and/or further acceleration of the phase transformation. This effect can lead to a shortening of the process time and hence of the process costs.

A further great advantage of the process according to the invention is that only small amounts of solvents, if any, are used.

A prerequisite for the phase transformation in the molecular solids is that very high relative speeds of the grinding media are employed. Particularly important in this context are the collisions between the grinding media, in which high energies are transmitted to the millbase. In the processes under tribochemical conditions, very high relative speeds of the grinding media of, for example, 14 m/s and more are desired and achieved. Normal ball mills work with relative speeds of usually below 5 m/s. The high energies are transmitted within a short time from the grinding media to the sample material or grinding material. These times can be derived if required from the relative speeds or the acceleration of the grinding media.

It is assumed that the process of tribochemical phase transformation is based essentially on processes in which high kinetic energies make up a significant part of the energy transmission $$E_{kin} = \tfrac{1}{2} m \cdot v^2$$

$E_{kin}$ kinetic energy
m ball mass
v ball speed

In a particularly preferred variant of the process, the phase transformation can take place in the "hotspots" (hot points) of the period of the plasma phase and/or in the post-plasma phase which follows directly. It is possible for phase transformations either to be induced or accelerated by the energies stored in the lattice defects. It is particularly advantageous when the phase transformation is brought about while the compound or compounds is/are present essentially as solids.

It is assumed that the principle of the process is based more on the collision of the millbase with the grinding media than on shear and frictional forces, as is customary in common equipment for particle comminution. The collision of the millbase with the grinding media can lead to comminution effects and deformation of the molecular solids used. Possible effects which can be caused by static pressure also play no role in the induction and/or acceleration of the phase transformation owing to the short collision times. Depending on the grinding material used and the grinding conditions selected—rotational speed and the resulting accelerations of the grinding media which may, for example, be about up to 50 G in the high-energy grinder used by way of example—a sufficient energy input to induce and/or accelerate the phase transformation can be achieved. The transformation conditions (grinder, rotational speed, ball acceleration, material of the grinding media) should be selected such that the process described is observed.

Common equipment for particle comminution which does not raise the high kinetic energies as transmitted by the high-energy ballmills are, for example, mortars and pestles, crossbeater mills, ballmills with relative speeds of the grinding media of about not more than 5 m/s, impact mills with relative speeds of about not more than 5 m/s, air-jet mills with relative speeds of about not more than 5 m/s, roller mills, grooved-disk mills, pinned-disk mills or bladed-disk mills, provided that they correspond to the current state of the art.

Particularly preferred mills for the tribochemical phase transformation according to the present invention are equipment which is considered to fall under the term of high-energy ballmilling. Further particularly preferred equipment is all of that which can transmit comparable high mechanical energies, especially high kinetic energies, or in which the formation of hot points and of the post-plasma phase can occur.

Particularly preferred equipment for use for the process according to the invention is all of that equipment which is referred to as high-energy ballmills. Further preferred equipment in the process according to the invention is that whose operation is based essentially on the same underlying principle as the known high-energy ballmills. The essential underlying principle shall be understood to mean that predominantly high mechanical energies, especially high kinetic energies, are transmitted, and/or so-called hotspots form in which a kind of plasma phase is present and/or a post-plasma phase follows.

Planetary ballmills, for example the Fritsch Pulverisette P7, agitated ballmills such as the Spex Mixer Mill 2000, but also the horizontal rotor ballmills, are particularly suitable for performing the process according to the invention. The list of mills is not complete and should merely be understood by way of example.

Particularly suitable grinding media (grinding cups and/or grinding balls) are those which consist of sintered corundum (density >3.8 g/cm$^3$), zirconium oxide (density 5.7 g/cm$^3$), stainless steel (density 7.8 g/cm$^3$), hardened steel (density 7.93 g/cm$^3$), tungsten carbide (density 14.89/14.7 g/cm$^3$), and also of materials which possess sufficient hardness and/or density to achieve the desired effect in the process according to the invention; examples here include alloys, fiber-reinforced ceramics or aluminum. Particularly preferred grinding media possess high masses; the high mass is preferably achieved via high densities of the material and/or an elevated atomic weight. The list of the grinding media and their materials in this context should not be understood to be exclusive.

Particular preference is given to short grinding times in order to rule out comminution of the millbase and/or to minimize the temperature effect when heating of the sample is undesired. This may be sensible, for example, in the case of easily decomposable or heat-sensitive substances. When heating of the sample is undesired, the energy input can be effected as a function of a certain temperature input. A setting of the temperature range may, for example, be as follows: at from −200° C. to −100° C. and from 25 to 50 G, from −100° C. to 0° C. and from 25 to 50 G, or from 0° C. to 15° C. and 25 to 50 G. Short grinding times are in the range of up to 60 minutes, and the grinding time can also be interrupted by an intermediate switching circuit. However, longer grinding times of over 60 minutes up to 48 hours are also conceivable, preference being given to grinding times of from a few minutes up to 10 hours. Even in the case of elevated grinding times, it may be advisable to perform the total grinding time in intervals.

The ratio of the grinding media (balls or other media) to the amount of sample may be from 100:1 to 50:1. For an economic process, it is appropriate to set the ratio of grinding media to samples below 10:1, in particular less than 5:1, preferably less than 2:1 and more preferably up to 1:10. In the latter ratios, the space-time yield is particularly high depending on the process batch.

It may be advantageous to use temperature programs, so that the performance of the phase transformation under preselected temperature conditions, for example also at constant temperature, is enabled. In the simplest case, this can be done, for example, by an intermediate switching circuit. In such cases too, energy inputs from 35 G, in particular above 40 G and preferably up to 50 G and higher are preferred.

Moreover, it may be appropriate to adjust the atmosphere above the millbase as required. Examples include defined moisture contents or defined atmospheres composed of solvent vapors or of a gas, inert gas, and mixtures thereof. It is also particularly appropriate to work under different pressures, for example at elevated pressures or else with reduced pressures, i.e. with application of a vacuum. It is obvious to the person skilled in the art that both the temperature control and the atmosphere or the pressures—elevated pressure or vacuum—are to be adjusted individually to the process. Here too, it is preferred to select an energy input from 35 G, in particular above 40 G and preferably up to 50 G and higher.

Particularly preferred solvents, solvent vapors or gases for establishing an atmosphere are $H_2O$, $CO_2$, argon, $N_2$, $O_2$, $NH_3$, hydrocarbons, chlorohydrocarbons, alcohols (methanol, ethanol, propanol), ketones, esters, ethers, amines, amides, halogens, HBr, HCl, HI. Quite generally, it is possible to use compounds which can be converted to the gas phase and mixtures thereof.

The process according to the invention can be carried out continuously, semicontinuously or batchwise. It is known to those skilled in the art that the aforementioned process parameters are adjusted with respect to one another individually for each process.

It is assumed that the phase transformation takes place in the so-called "hotspots" (hot points) of the period of the plasma phase and/or in the post-plasma phase which follows directly. The phase transformation can also be induced by one of the aforementioned events and, overall, proceed over a prolonged period or else be accelerated by the event. Moreover, the phase transformations may be induced at the interfaces of the molecular solids; the phase transformation can then continue, for example, by migration through the solid. In the process according to the invention, it is also possible to establish equilibria between phases of molecular solids. The transformation of a phase to a further phase, which can pass through further intermediate phases, is likewise possible. In a particularly preferred variant, the entire solid is transformed essentially uniformly into one phase. This does not exclude the possibility that the solids may possess the defects commonly known for them. Typically, the phase transformation is brought about while the starting compound is present essentially as a solid. In general, the temperature is not regulated.

It is also assumed that the process according to the invention influences the weak intermolecular interactions. These may, for example, be hydrogen bonds or further intermolecular interactions which are based on dipole-dipole or van der Waals interactions. Phase transformations shall be understood not to mean classic reactions or syntheses in which, for example, covalent bonds are broken and/or newly formed. The invention also encompasses those transformations of molecular solids which are based on a transformation which is based on processes in a defined atmosphere.

The process according to the invention may be applied to organic or inorganic molecules, which also include the macromolecules. It is also possible to use mixtures of inorganic and organic molecules.

Molecular solids are not restricted to monomolecular solids; they also extend to cocrystals, i.e. to solids from the field of crystal engineering, in which case solids from the field of crystal engineering as described above may be present. In addition, molecular solids are also understood to mean those which have solvents intercalated in the crystal lattice, whether it be randomly, as adducts or stoichiometrically at fixed lattice sites.

The solids consisting essentially of organic and/or inorganic molecules and also of possible mixtures are, for example, synthetic or natural, medicament and/or cosmetic active ingredients, excipients, food additives, pigments, dyes, impregnating agents, antioxidants, preservatives; molecular solids which find use in washing compositions, detergents, surfactants; substances which are used for data storage or, for example, molecular magnets. Active substances from the field of crop protection include in particular fungicides, pesticides, insecticides, etc.

In principle, useful molecular solids for the process according to the invention are those which may be present in at least two different phases of which at least one is a crystalline phase.

It is also possible to use mixtures of organic and inorganic compounds in the process according to the invention, and also complexes, salts, cocrystals, mixed phases or mixed crystals thereof.

It is also appropriate to use mixtures of molecular solids and excipients. Excipients should be understood to mean in particular the excipients used in the pharmaceutical industry and all excipients which can play a role in the later further processing of the molecular solids. For example, it may be advantageous to subject a finished formulation composed of molecular solids and excipients directly to the process and then to compress them.

In principle, preference is given to transformations which provide a content of the desired molecular solid in order to achieve the desired effect in the particular case.

In addition, preference is given to processes in which a phase transformation or phase transformations take(s) place between polymorphs. Particular preference is given to a transformation degree of at least 80% based on the entirety of the original phases. The degree of transformation can be determined, for example, by X-ray powder diffractometry.

It is also possible to use amorphous glasslike phases in the process according to the invention and convert them to crystalline phases. Crystallinities of over 80% are desired in the molecular solids. Particular preference is given to generating only a single polymorph.

Variants of the processes according to the invention also enable the transformation of polymorphs not present in phase-pure form to phase-pure polymorphs.

The polymorphs, hydrates and/or adducts obtainable by means of the process according to the invention may consist of at least one organic or inorganic compound, but also of a multitude of compounds, as may be the case, for example, in solvates, cocrystals, complexes, salts, mixed crystals.

The molecular solids which are obtainable by the process according to the invention may, for example, find use in the preparation of a medicament. The use of the process according to the invention here is advantageous, since it enables a solvent-free preparation.

A requirement that many medicaments must/should satisfy is, for example, that they are present in essentially solvent-free form. A significant advantage of the process according to the invention is that solvates, solvent adducts or hydrates of the active ingredients which are obtained, for example, from a preceding, for example purifying, crystallization step can now be converted to a stable solvent- and hydrate-free polymorph. Specifically for this use, it is found to be particularly advantageous when a defined atmosphere, air moisture content or vacuum/elevated pressure with temperature control of the process is predefined.

In the case of preparation of medicaments, it is particularly advantageous that a later phase transformation in the homogenization, the compaction, the granulation or, for example, in the tablet pressing of the pharmaceutical formulations is very improbable, and hence the predefined product specification, for example its bioavailability, can be ensured when active substances obtained in accordance with the invention are used. In addition, the homogenization or grinding of the compound can certainly be dispensed with in many cases.

Further very advantageous aspects of the procedure according to the invention are high space-time yields and high absolute yields. A significant and particularly favorable feature of many molecular solids which were subjected to the process according to the invention is their elevated density compared to the starting material. It is particularly desired to isolate molecular solids with the greatest density.

It is assumed that, for the examples in which the density difference is sufficiently great and the strength of all inter- and intramolecular interactions possibly does not dominate the phase transformation, the tighter packings are formed when sufficient energy input takes place simultaneously.

It is also possible to transform solvates or solvent adducts to stable hydrates of the corresponding compounds. This can be enabled by a controlled process in which, for example, a vacuum is first applied and then a certain moisture content, if desired in conjunction with temperature control, is programmed. In a particularly preferred variant, the temperature is not regulated.

Moreover, it is also possible to transform solvates or solvent adducts to other solvates or solvent adducts of the corresponding compounds, which, for example, are more stable or pharmacologically safer. This can be enabled by a controlled process in which, for example, a vacuum is first applied and then certain solvent vapors or mixtures thereof with air moisture, if desired in conjunction with temperature control, are programmed.

In addition, it is possible to convert solvates or solvent adducts to stable solvent-free molecular solids of the corresponding compounds. This can be a controlled process in which, for example, a vacuum is first applied and/or a certain atmosphere which enables the removal of the solvent molecules is then programmed. If appropriate, this can be provided in conjunction with temperature control. Preferred atmospheres are gases (inert gases) and solvent vapors, and also mixtures thereof. Particular preference is given to $N_2$, argon, $CO_2$, air.

For the solids obtained in accordance with the invention, it is possible, for example, to use the polymorphs prepared in accordance with the invention as an active substance, excipient, pigment, dye, magnetic material, optically active material, high-energy material, wash-active detergent, storage medium or food additive.

A particular advantage of the process according to the invention is that loss-free or almost loss-free process control with relatively low production costs is enabled. The process is significantly more environmentally friendly than solvent-dependent phase transformations.

Moreover, high throughputs are also possible with these processes. Nowadays, equipment is already available which has a capacity of up to 400 L, but even greater capacities are conceivable.

The examples which follow serve to illustrate phase transformations carried out by way of example on compounds selected by way of example. They are merely to be understood as possible procedures detailed by way of example without restricting the invention to their contents.

The detection of the particular modification/form was conducted with X-ray powder diffractometry: X-ray diffractometer: SToe STADI P transmission diffractometer, $CuK\alpha_1$: 1.54060 Å, linear position-sensitive detector, measurement range 5-40°2Theta, step width 0.01°2Theta, measurement time 960 sec/step.

Example 1

2-Sulfanilamido-4-methylpyrimidine, INN: sulfamerazine: Sulfamerazine is administered as a combination preparation together with trimethropin as an antibiotic. The sulfonamide intervenes in the synthesis of folic acid and displaces the p-amino acid there. As a result, it competitively inhibits the first step of folic acid formation of the bacteria. This disruption prevents the multiplication of the bacteria.

To date, two polymorphs of sulfamerazine are known in the literature. The form 1 with the unit cell $Pn2_1a$ has a melting point of about 235° C. The form 2 has the unit cell Pbca and is converted to the more stable form 1 at about 170° C. It is known that neither polymorphic form undergoes a transformation to another phase in the course of grinding. The density of form 1 is reported to be 1.35 g/cm³ and that of form 2 to be 1.43 g/cm³).

Form 2 is preferred, since it releases the sulfamerazine better and is less hygroscopic. However, form 2 can be obtained within acceptable crystallization times only from undesirable solvents, for example acetonitrile or a mixture of water and acetonitrile. In industrial scale processes, conditions have to date been maintained which lead only to the formation of form 1.

It was possible to convert sulfamerazine of form 1 as a solid fully to form 2. The transformation was detected by means of X-ray powder diffractometry.

High-energy mill: Fritsch Pulverisette 7;

Grinding cup: hardened steel, volume 10 ml;

Balls: hardened steel, 8 g per ball, 4 balls per 10 ml grinding cup (1.1-1.4)

Revolutions: 800 rpm

Amount of substance:

1.0 g in experiments 1.1, 1.2, 1.3 and 1.4;

10.0 g in experiments 1.5, 1.6, 7 balls in 40 ml grinding cups 15.0 g in experiment 1.7, 2 balls of approx. 7.43 in 40 ml grinding cups.

Time: see particular experiments

Temperature control: no temperature control

Example 1.1

1.0 g of the commercial sulfamerazine form 1 was ground under normal atmosphere at 800 rpm for 1 hour. Virtually full conversion of form 1 to the desired form 2 was obtained.

Example 1.2

1.0 g of the commercial sulfamerazine form 1 was ground under normal atmosphere at 800 rpm for 5 minutes. The diffractogram of the analyzed sample exhibits significantly broadened reflections which are, however, still attributable to form 1.

Example 1.3

1.0 g of the commercial sulfamerazine form 1 was ground under normal atmosphere at 800 rpm for 15 minutes. The diffractogram of the analyzed sample exhibits very broad reflections which indicate an increased content of amorphous fractions. However, the reflections observed are still attributable to form 1.

Example 1.4

1.0 g of the commercial sulfamerazine form 1 was ground under normal atmosphere at 800 rpm for 30 min minutes. The diffractogram of the analyzed sample exhibits very narrow reflections, all of which are attributable to form 2.

A comparison of the results of Example 1.1 with those of Example 1.3 shows that a prolonged process time only causes broadening of the reflections of form 2, which is attributable to a decrease in the crystallinity of the sample.

Example 1.5

10.0 g of the commercial sulfamerazine form 1 were ground under normal atmosphere at 800 rpm for 15 minutes. The diffractogram of the analyzed sample exhibits very broad reflections which indicate an increased content of amorphous fractions. The reflections observed are those of form 1.

Example 1.6

10.0 g of the commercial sulfamerazine form 1 were ground under normal atmosphere at 800 rpm for 30 min minutes. The diffractogram of the analyzed sample exhibits very narrow reflections, all of which are attributable to form 2.

Example 1.7

15.0 g of the commercial sulfamerazine form 1 were ground under normal atmosphere with 2 balls at 800 rpm for 120 and 180 min minutes. The diffractogram of the analyzed sample shows the formation of form 2.

When the sample is ground further up to a total grinding time of 60 minutes, the reflections of form 2 measured again become broader.

Example 2

5-Acetamido-1,3,4-thiadiazole-2-sulfonamide, INN: acetazolamide: The sulfonamide group of the active ingredient is essential for its action as a carboanhydrase inhibitor and hence causes in particular increased excretion of water and salts through the kidneys. Occasionally, it is used as an additional epileptic drug in epilepsy which is difficult to treat.

Known polymorphic forms of acetazolamide are polymorph 1 with unit cell $P2_1/n$ and polymorph 2 with the unit cell P1. Even though polymorph 1 is the metastable phase at room temperature, it is not transformed over a prolonged period. Polymorph 2 is the thermodynamically stable polymorph at room temperature. Polymorph 1 can be obtained by heating polymorph 2 which is converted to polymorph 1 at 120-148° C. The literature (U. Griesser, A. Burger, K. Brandstätter; J. Pharm. Sciences, 1997, 86(3), 352-358) discloses that polymorph 1 is not converted back to polymorph 2 again by applying mechanical stress in the form of grinding or pressure or by storing it within a period of over 5 years. Nor has the transformation of polymorph 2 to polymorph 1 under mechanical stress been observed to date, even though polymorph 1 possesses a greater density compared to polymorph 2 (polymorph 1: 1.77 $g/cm^3$; polymorph 2:1.749/1.751 $g/cm^3$).

It was possible to induce virtually full transformation of polymorph 2 to polymorph 1. The transformation was detected by means of X-ray powder diffractometry.

High-energy mill: Fritsch Pulverisette 7;

Grinding cup: hardened steel, volume 10 ml;

Balls: hardened steel, 8 g per ball, 4 balls per 10 ml grinding cup

Revolutions: 800 rpm in Experiments 2.1, 2.2

400 rpm in Experiment 2.3

Amount of substance: 1.0 g

Time: see particular experiments

Experiment 2.1

1.0 g of polymorph 2 of acetazolamide was subjected to the process at 800 rpm for 1 hour. The acetazolamide converted virtually fully to polymorph 1 was isolated.

Experiment 2.2

1.0 g of polymorph 2 of acetazolamide was subjected to the process at 800 rpm for 5 minutes. The diffractogram of the analyzed sample exhibits very broad reflections which indicate an increased content of amorphous fractions. The reflections observed are attributable to the polymorph 2 used.

Experiment 2.3

As Experiment 2.2, except that the acetazolamide was subjected to the process at 800 rpm for 30 minutes. At a treatment time of 30 min, polymorph 1 is isolated.

Experiment 2.4

As Experiment 2.2, except that the acetazolamide was subjected to the process at 800 rpm for 45 minutes. At this treatment time, polymorph 1 is likewise isolated, but the reflections observed here are somewhat narrower than at a treatment time of 30 min.

Experiment 2.5

1.0 g of polymorph 2 of acetazolamide was subjected to the process at 400 rpm for 30 minutes. The diffractogram of the analyzed sample exhibits very broad reflections which indicate an increased content of amorphous fractions. The reflections observed are attributable to the polymorph 2 used.

Experiment 2.6

As Experiment 2.5, except that the acetazolamide was subjected to the process at 400 rpm for 60 minutes. Under these conditions too, no phase transformation is observed.

Example 3

Chlorpropamide: Chlorpropamide is a medicament against diabetes mellitus (antidiabetic) and belongs to the group of the sulfonylureas. The sulfonamide group of chlorpropamide is essential for its action as a carboanhydrase inhibitor. The action of the medicament is based on an increased release of insulin which in turn lowers the blood sugar level.

Chlorpropamide is commercially available as form A. The metastable form C, in contrast, can be obtained by heating form A at 115° C. over a period of 3 hours. K. Morris et al. disclose that form A exhibits detectable phase transformations under none of the mechanical stresses listed, whereas form C, when it is subjected to the mechanical stresses, has partial phase transformation to form A.

The process according to the invention can convert form A partly to form C and form C fully to form A.

High-energy mill: Fritsch Pulverisette 7;
Grinding cup: hardened steel, volume 10 ml;
Balls: hardened steel, 8 g per ball, 4 balls per 10 ml grinding cup
  Revolutions: 800 rpm
  Amount of substance: 1.0 g
  Time: see particular experiments

Experiment 3.1

Chlorpropamide form A was treated under the conditions listed over a period of 1 hour. In addition to a significant broadening of the reflections, partial transformation to form C can be observed.

Experiment 3.2

Chlorpropamide form C was ground under the conditions listed over a period of 15 minutes. In addition to a significant broadening of the reflections, a clearly perceptible incipient transformation to form A can be observed.

Experiment 3.3

Chlorpropamide form C was ground under the conditions listed over a period of 60 minutes. The sample has been transformed fully to form A.

What is claimed is:

1. A process for inducing and/or accelerating at least one phase transformation in solid organic molecules, wherein the solid organic molecules are subjected to a tribochemical treatment to result in a phase transformation of the solid organic molecules, and wherein the phase transformation is achieved essentially by means of transmission of high kinetic energies of 20 G or higher.

2. The process as claimed in claim 1, wherein the phase transformation is achieved essentially by means of transmission of high mechanical energies.

3. The process as claimed in claim 1, wherein the phase transformation is achieved essentially by means of transmission of high kinetic energies of 35 G to 50 G and higher.

4. The process as claimed in claim 1, wherein the transformation is to a crystalline phase.

5. The process as claimed in claim 1, wherein the phase transformation is induced at the interfaces of the solid.

6. The process as claimed in claim 1, wherein the transformation takes place between two polymorphs.

7. The process as claimed in one claim 1, wherein the transformation takes place from an amorphous or glasslike phase to one or more crystalline phases.

8. The process as claimed in claim 1, wherein a solid not present in phase-pure form is converted to a phase-pure polymorph.

9. The process as claimed in claim 1, wherein the solid organic molecules are mixtures of solid organic molecules.

10. The process as claimed in claim 1, wherein a semicontinuous process is effected.

11. The process as claimed in claim 1, wherein it is effected under a defined atmosphere.

12. The process as claimed in claim 1, wherein it is effected under a defined pressure.

13. The process as claimed in claim 1, wherein it is effected under temperature control.

14. The process as claimed in claim 1, wherein the solid possesses a greater density after the phase transformation.

15. A method of using high-energy mills for performing phase transformations comprising:
  providing a high energy mill,
  providing solid organic molecules, and
  subjecting the solid organic molecules to a tribochemical treatment,
  wherein the phase transformation is achieved essentially by means of transmission of high kinetic energies of 20 G or higher.

16. The method of claim 15, wherein transmission of high kinetic energies includes providing grinding media moving at a velocity of 14 m/s and greater in the high energy mill.

17. A method of inducing or promoting a phase transition in an active pharmaceutical ingredient comprising:
  providing an active pharmaceutical ingredient; and
  transmitting high kinetic energies to the active pharmaceutical ingredient;
  wherein the phase transformation is achieved essentially by means of transmission of high kinetic energies of 20 G or higher.

18. A method of inducing or promoting a phase transition in co-crystal comprising:
  providing a co-crystal; and
  transmitting high kinetic energies to the co-crystal;
  wherein the phase transformation is achieved essentially by means of transmission of high kinetic energies of 20 G or higher.

19. A method of inducing or promoting a phase transition in an organic molecule comprising:
  providing an organic molecule; and
  transmitting high kinetic energies of 20 G or higher to the organic molecule to effect a phase transformation of the organic molecule;
  wherein the organic molecule after phase transformation has a phase which is a co-crystal.

20. A method of inducing or promoting a phase transition in an organic molecule comprising:
  providing an organic molecule; and
  transmitting high kinetic energies of 20 G or higher to the organic molecule to effect a phase transformation of the organic molecule,
  wherein the phase transition is to a crystalline phase and the organic molecule in the crystalline phase is a co-crystal.

* * * * *